United States Patent
Lustig et al.

(10) Patent No.: US 6,555,326 B1
(45) Date of Patent: Apr. 29, 2003

(54) NUCLEAR HORMONE RECEPTOR FLUORESCENCE POLARIZATION ASSAY

(75) Inventors: Kevin Lustig, South San Francisco, CA (US); Patrick Baeuerle, South San Francisco, CA (US); Holger Beckmann, South San Francisco, CA (US); Jin-Long Chen, South San Francisco, CA (US); Bei Shan, South San Francisco, CA (US)

(73) Assignee: Tularik Inc., South San Francisco, CA (US)

( * ) Notice: Subject to any disclaimer, the term of this patent is extended or adjusted under 35 U.S.C. 154(b) by 0 days.

(21) Appl. No.: 08/975,614

(22) Filed: Nov. 21, 1997

(51) Int. Cl.[7] .................. G01N 33/52; G01N 33/53; G01N 33/566
(52) U.S. Cl. ........................ 435/7.8; 435/7.1
(58) Field of Search ............ 530/350; 435/7.1, 435/7.8

(56) References Cited

U.S. PATENT DOCUMENTS 6,020,141 A  * 2/2000 Pantoliano et al.

FOREIGN PATENT DOCUMENTS

WO    WO 9710337 A1    3/1997

OTHER PUBLICATIONS

Heery Et Al. (1997) Nature 387:733–736.*
Torchia Et Al. (1997) Nature 387:677–684.*
Montming (1997) Nature 387:654–655.*
Mathis (1995) Clinical Chemistry 41:1391–1397.*
Mangelsdorf Et Al. (1995) Cell 83:841–850.*

* cited by examiner

Primary Examiner—Michael Pak
(74) Attorney, Agent, or Firm—Richard Aton Osman

(57) ABSTRACT

Methods for identifying modulators of nuclear hormone receptor function comprise the steps of (a) forming a mixture comprising a nuclear hormone receptor, a peptide sensor and a candidate agent, but not a natural coactivator protein of the receptor, wherein the sensor provides direct, in vitro binding to the receptor under assay conditions; (b) measuring an agent-biased binding of the sensor to the receptor; and (c) comparing the agent-biased binding with a corresponding unbiased binding of the sensor to the receptor. In particular embodiments, the sensor comprises an amphipathic alpha helix nuclear hormone interacting domain comprising a recited nuclear hormone transcriptional coactivator motif sequence, the sensor is present at sub-micromolar concentration, the binding reaction occurs in solution, the sensor comprises a fluorescent label and the measuring step comprises detecting fluorescence polarization of the label. Reagents include labeled sensor peptides and reaction mixtures consisting essentially of nuclear hormone receptor, a peptide and a candidate agent.

18 Claims, 4 Drawing Sheets ns of the receptors sufficient to provide differential sensor binding in the presence and absence of a corresponding receptor ligand, agonist and/or antagonist.

NUCLEAR HORMONE RECEPTOR FLUORESCENCE POLARIZATION ASSAY

FIELD OF THE INVENTION

The field of this invention is screens for drugs effecting nuclear hormone receptor function.

BACKGROUND

Nuclear hormone receptors comprise a large, well-defined family of ligand-activated transcription factors which modify the expression of target genes by binding to specific cis-acting sequences (Laudet et al., 1992, EMBO J, Vol, 1003–1013; Lopes da Silva et al., 1995, TINS 18, 542–548; Mangelsdorf et al., 1995, Cell 83, 835–839; Mangelsdorf et al., 1995, Cell 83, 841–850). Family members include both orphan receptors and receptors for a wide variety of clinically significant ligands including steroids, vitamin D, thyroid hormones, retinoic acid, etc. Ligand binding is believed to induce a conformational change in the receptors and promote their association with transcriptional coactivators, which are a diverse group of large nuclear proteins (Glass et al., 1997, Curr Opn Cell Biol 9, 222–232), which may share a signature sequence motif (Heery et al., 1997, Nature 733–736). The resulting complex then binds high affinity sites in chromatin and modulates gene transcription.

The classic approach to identifying agonists or antagonists of nuclear hormone receptors is the ligand displacement assay, where the displacement of radiolabeled ligand by candidate agents is detected. An alternative approach is a cell-based transcription assay for expression of a reporter of nuclear hormone receptor activation (e.g. Evans et al. (1991) U.S. Pat. No. 5,071,773). More recently, a gel-based coactivator dependent receptor ligand assay (Krey et al., 1997, Mol Endocrinol 11, 779–791) has been used to identify ligands of peroxisome proliferator-activated receptors (PPARs), which are nuclear hormone receptors activated by a variety of compounds including hypolipidemic drugs. Unfortunately, these various assays suffer from a number of limitations including a required known ligand and time, labor and resource intensive cell-based and gel-based methods, respectively.

SUMMARY OF THE INVENTION

The invention provides methods and compositions for efficient screening of modulators of nuclear hormone receptor function, without the use of cell- or gel-based steps. The methods are amenable to automated, cost-effective high throughput screening of chemical libraries for bioactive compounds.

In one embodiment, the invention provides in vitro methods comprising the steps of (a) forming a mixture comprising a nuclear hormone receptor, a peptide sensor and a candidate agent, but not a natural coactivator protein of the receptor, wherein the sensor provides direct, in vitro binding to the receptor under assay conditions; (b) measuring an agent-biased binding of the sensor to the receptor; and (c) comparing the agent-biased binding with a corresponding unbiased binding of the sensor to the receptor, wherein a difference between the biased and unbiased bindings indicates that the agent modulates a receptor function. In particular embodiments, the sensor comprises an amphipathic alpha helix nuclear hormone interacting domain comprising a nuclear hormone transcriptional coactivator motif sequence. To ensure specificity and optimize binding, the sensor is generally present at sub-micromolar concentration and the binding reaction occurs in solution. In a preferred embodiment, the sensor comprises a fluorescent label and the measuring step comprises detecting fluorescence polarization of the label.

The invention also provides reagents such as labeled sensor peptides and reaction mixtures consisting essentially of nuclear hormone receptor, a peptide and a candidate agent, wherein the peptide provides direct, in vitro ligand-dependent binding to the receptor, especially in which the binding is enhanced in the presence of the agent.

DETAILED DESCRIPTION OF THE INVENTION

Figure 1:
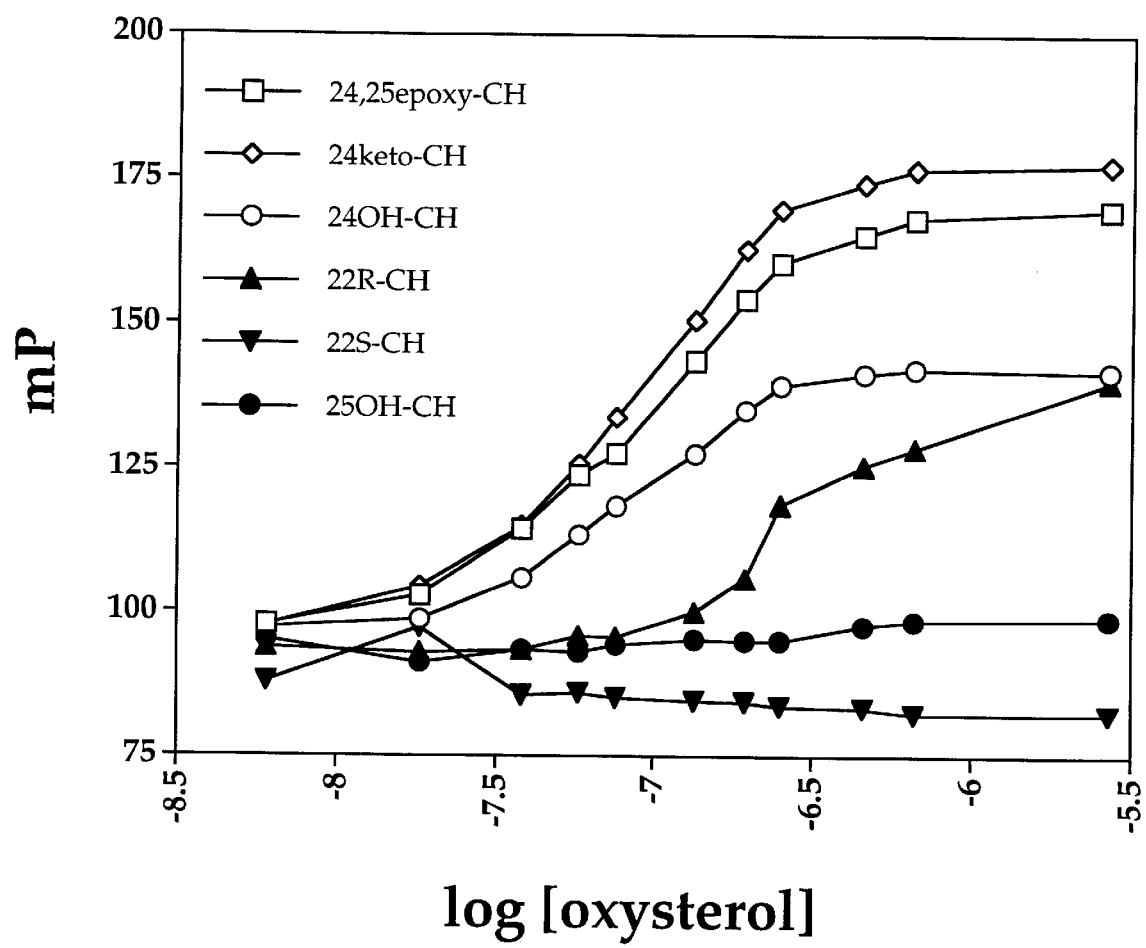
FIG. 1. LXR activation dose response with oxysterol ligands in fluorescent polarization assay with TUK-1391 sensor.

The methods generally employ a mixture comprising three components: a nuclear hormone receptor, a peptide sensor and a candidate agent, in amounts effective to measure the targeted interactions. Many natural nuclear hormone receptors are modular proteins with discrete functional domains, including a ligand binding domain; see Laudet et al.; Lopes da Silva et al.; Mangelsdorf et al.; supra. The subject receptors encompass such full-length receptors as well as portions of the receptors sufficient to provide differential sensor binding in the presence and absence of a corresponding receptor ligand, agonist and/or antagonist. Such portions generally comprise at least the ligand binding domain of the receptor. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, N.Y.) or that are otherwise known in the art. Exemplary nuclear hormone receptors and corresponding target therapeutic application are listed in Table 1.

TABLE 1

Exemplary nuclear hormone receptors, form (M = monomeric, D = heterodimeric, H = homodimeric), tissue expression and target therapeutic application

| Receptor | Form | Tissue Expression | Target Therapeutic Application |
| --- | --- | --- | --- |
| NURR1 | M/D | Dopaminergic Neurons | Parkinson's Disease |
| RZRβ | M | Brain (Pituitary), Muscle | Sleep Disorders |
| RORα | M | Cerebellum, Purkinje Cells | Arthritis, Cerebellar Ataxia |
| NOR-1 | M | Brain, Muscle, Heart, Adrenal, Thymus | CNS Disorders, Cancer |
| Rev-ErbAβ | H | Brain, Muscle, Spleen | CNS Disorders |
| T1x | H | Embryonic and Adult Brain | CNS Disorders |
| NGFI-Bβ | M/D | Brain | CNS Disorders |
| HZF-2α | H | Hippocampus | CNS Disorders |
| COUP-TFα | H | Brain | CNS Disorders |
| COUP-TFβ | H | Brain | CNS Disorders |
| COUP-TFγ | H | Brain | CNS Disorders |
| Nur77 | M/D | Brain, Thymus, Adrenals | CNS Disorders |
| LXRα | D | Liver, Kidney, Spleen, Adrenals | Hypercholesterolemia |
| COR | M | Liver, Pancreas | Hypercholesterolemia |
| Rev-ErbAα | H | Muscle, Brain (Ubiquitous) | Obesity |
| HNF4α | H | Liver, Kidney, Intestine | Diabetes |
| TOR | M | Thymus, T Cells, Lymphoma | Immune Disorders |
| MB67α | D | Liver | Metabolic Disorders |
| SHP | D | Liver, Heart, Pancreas | Metabolic Disorders |
| FXR | D | Liver, Kidney | Metabolic Disorders |
| SF-1 | M | Gonads, Pituitary | Metabolic Disorders |
| LXRβ | D | Kidney (Ubiquitous) | Metabolic Disorders |
| GCNF | M/H | Testes, Ovary | Infertility |
| TR2-11α,β | H | Testes | Infertility, Contraception |
| TR4 | H | Testes | Infertility, Contraception |
| ERRα,β | M | Placenta | Infertility |
| DAX-1 | M | Testes, Adrenals, Ovary, Liver | Adrenal Hypoplasia, Hypogonadism |

The mixture also includes a peptide sensor which provides direct, in vitro, significant assay detectable binding to the receptor under assay conditions. Accordingly, the sensor obviates the need to include a natural coactivator protein of the receptor in the mixture. The sensor comprises a receptor binding sequence, generally $L_1X_1X_2L_2L_3$, wherein $L_1$–$L_3$ are independently selected from hydrophobic amino acids, preferably leucine or isoleucine, more preferably leucine; and $X_1$–$X_2$ are independently selected from any amino acid, preferably any natural amino acid. The sensor region comprising this sequence generally forms an amphipathic alpha helix. Such sequences may be natural coactivator protein motif sequences, derived from coactivator motif sequences or consensus sequences thereof, e.g. by step-wise mutational analysis, and/or from screens of purely or partly synthetic sequences, e.g. randomizing residues and selecting for receptor binding. The sensors are of length and sequence sufficient to effect the requisite specific binding, generally 50 or fewer, preferably 24 or fewer, more preferably 12 or fewer residues in length. Accordingly, panels of predetermined or randomized candidate sensors are readily screened for receptor binding. For example, in the high-throughput fluorescent polarization assay (below), candidate sensors demonstrating specific binding are conveniently identified by enhanced fluorescent polarization, generally an increase of at least about 5, preferably at least about 10, more preferably at least about 20 millipolarization units under optimized binding assay conditions.

Figure 2:
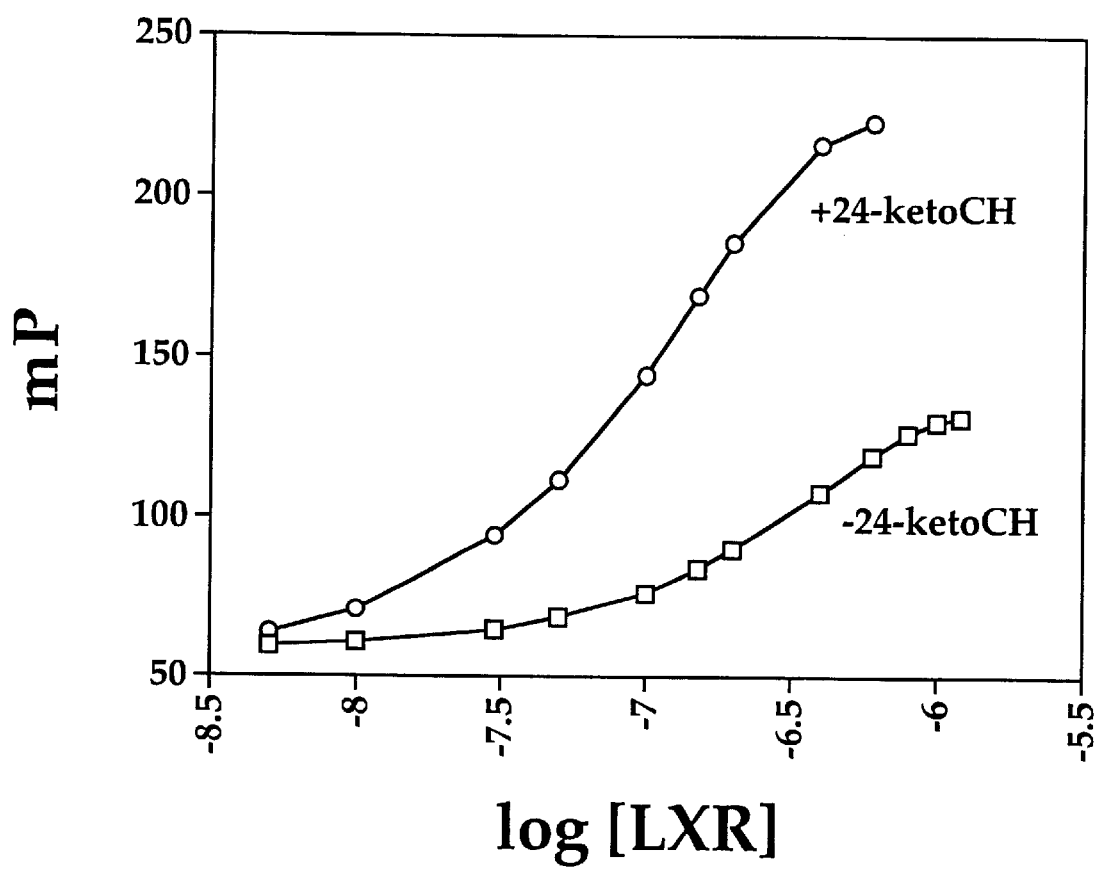
FIG. 2. Dose response showing 24-ketocholesterol ligand (2 $\mu$M) increases LXR receptor affinity for labeled peptide sensor in fluorescent polarization assay.
Figure 3:
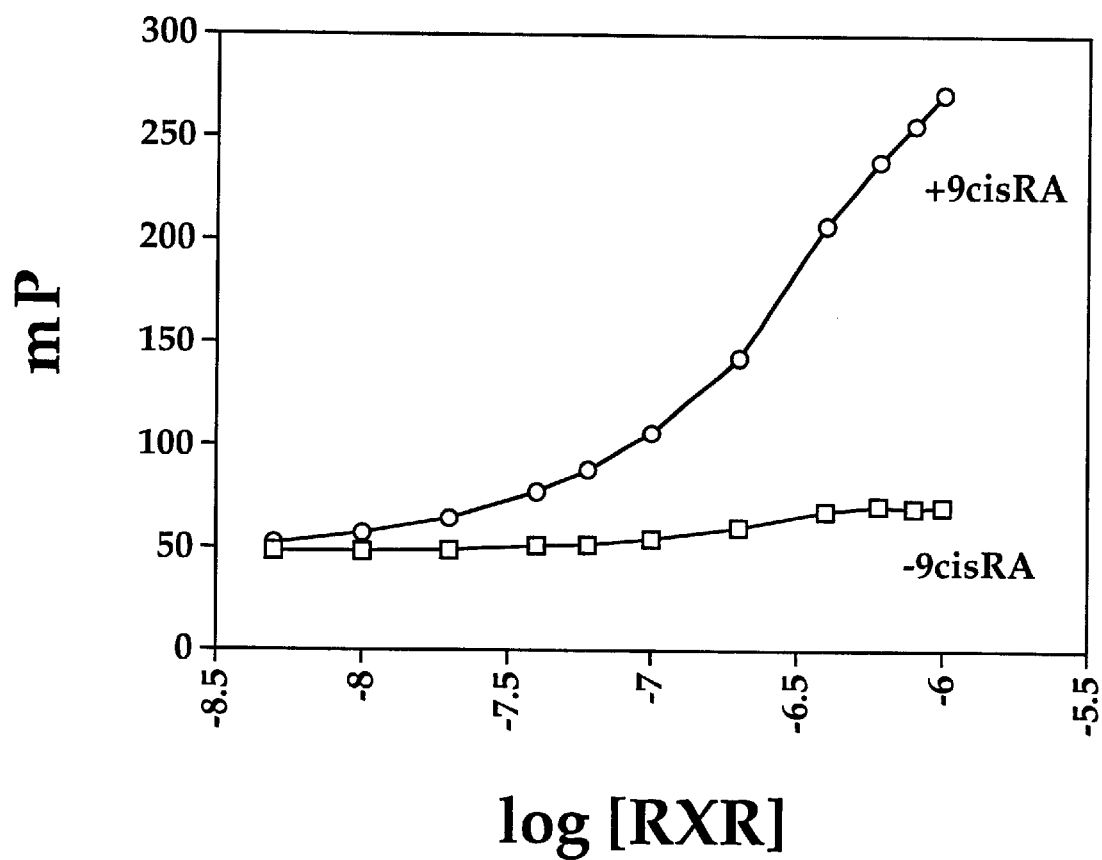
FIG. 3. Dose response showing 9-cis-retinoic acid ligand (1 $\mu$M) increases RXR receptor affinity for labeled peptide sensor in fluorescent polarization assay.
Figure 4:
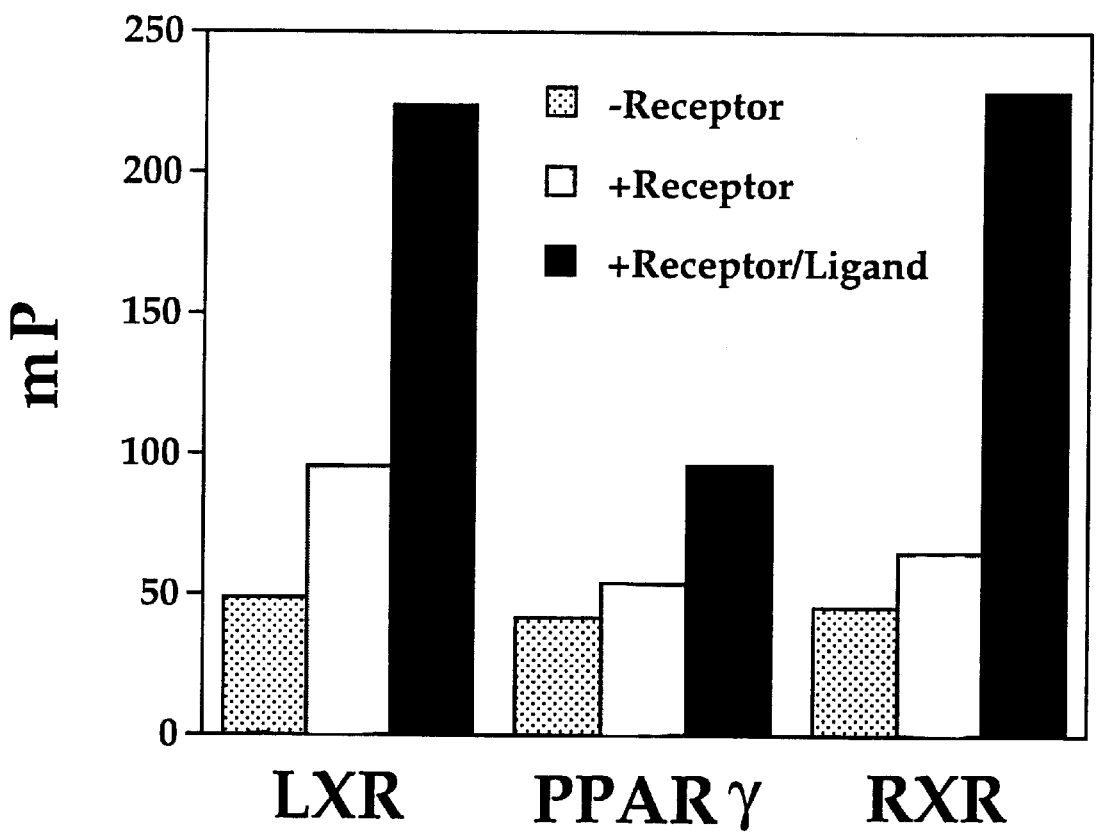
FIG. 4. Fluorescent polarization NRH agonist assay validation for LXR/24-ketocholesterol ligand (2 $\mu$M), PPAR$\gamma$/BRL49653 (1 $\mu$M) and RXR/9-cis-retinoic acid ligand (1 $\mu$M) with TUK-1391 sensor.

In a particular embodiment, the sensors demonstrate ligand, agonist and/or ligand dependent binding i.e. the sensor differentially binds the receptor in the presence and absence of such ligand/agonist/antagonist, generally differential binding of at least 10/10%, preferably at least 100/50%, more preferably at least 1,000/90%, respectively. Accordingly, panels of predetermined or randomized candidate sensors are readily screened for differential binding, as exemplified in FIGS. 2 and 3 for two exemplary receptor/ligand pairs. Analogously, differential binding is conveniently demonstrated using known agonists or antagonists of targeted receptors. For orphan receptors, it is often convenient to prescreen known ligands for pseudo-ligands or surrogates which selectively bind the ligand binding domain. Alternatively, agonists and/or antagonists may be identified by screening predetermined or randomized candidate labeled peptides for sensors which demonstrate assay detectable receptor binding, and then screening for agents which increase/decrease the binding of the identified sensor to the receptor, i.e. agonists/antagonists, respectively.

Exemplary sensors and binding data are shown in Table 2.

TABLE 2

Sensors Activity: Fluorescent Polarization Assay

| Sensor | Label | Sequence | LXR | PPARγ | RXR |
| --- | --- | --- | --- | --- | --- |
| SRC-1 632–640 | | | | | |
| TUK-1384 | F- | KLVQLLTTT SEQ ID NO: 1 | I | O | O |
| TUK-1386 | F-G- | KLVQLLTTT | I | O | O |

TABLE 2-continued

Sensors Activity: Fluorescent Polarization Assay

| Sensor | Label | Sequence | LXR | PPARγ | RXR |
|---|---|---|---|---|---|
| TUK-1385 | R- | KLVQLLTTT | II+ | I | II+ |
| TUK-1387 | R-G- | KLVQLLTTT | + | O | II |
| SRC-1 689–696 | | | | | |
| TUK-1370 | F- | ILHRLLQE | II | O | II |
| TUK-1371 | R- | ILHRLLQE SEQ ID NO: 2 | IV | I+ | IV |
| TUK-1373 | R-G- | ILHRLLQE | II | O | II+ |
| SRC-1 748–755 | | | | | |
| TUK-1390 | F- | LLRYLLDK SEQ ID NO: 3 | IV | II | II+ |
| TUK-1392 | F-G- | LLRYLLDK | II+ | I | I |
| TUK-1391 | R- | LLRYLLDK | IV | II+ | IV |
| TUK-1393 | R-G- | LLRYLLDK | III+ | I | II+ |
| SRC-1 748–754 | | | | | |
| TUK-1453 | R- | LLRYLLD SEQ ID NO: 4 | III | I | I+ |
| SRC-1 749–754 | | | | | |
| TUK-1455 | R- | LRYLLD SEQ ID NO: 5 | IV | I+ | I |
| SRC-1 748–753 | | | | | |
| TUK-1457 | R- | LLRYLL SEQ ID NO: 6 | II | + | I |
| SRC-1 749–753 | | | | | |
| TUK-1459 | R- | LRYLL SEQ ID NO: 7 | III | I | O |
| SRC-1 748–756 | | | | | |
| TUK-1472 | R- | LLRYLLDKD SEQ ID NO: 8 | IV | II | IV |
| SRC-1 747–756 | | | | | |
| TUK-1473 | R- | QLLRYLLDKD SEQ ID NO: 9 | IV | I+ | I+ |
| SRC-1 746–756 | | | | | |
| TUK-1474 | R- | HQLLRYLLDKD SEQ ID NO: 10 | IV | O | I |
| SRC-1 1427–1440 | | | | | |
| TUK-1395 | F- | PQAQQKSLLQQLLT SEQ ID NO: 11 | O | O | O |
| TUK-1397 | F-G- | PQAQQKSLLQQLLT | O | O | O |
| TUK-1398 | R-G- | PQAQQKSLLQQLLT | O | O | O |
| SRC-1 1434–1441 | | | | | |
| TUK-1380 | F- | LLQQLLTE SEQ ID NO: 12 | II+ | O | O |
| TUK-1382 | F-G- | LLQQLLTE | II+ | O | O |
| TUK-1381 | R- | LLQQLLTE | IV | I+ | I+ |
| TUK-1383 | R-G- | LLQQLLTE | II | O | O |
| RIP-140 496–506 | | | | | |
| TUK-1374 | F- | VTLLQLLLG | IV | I | O |
| TUK-1376 | F-G- | VTLLQLLLG SEQ ID NO: 13 | II+ | + | O |
| TUK-1375(1433) | R- | VTLLQLLLG | IV | I | O |
| TUK-1377 | R-G- | VTLLQLLLG | II | I | + |
| Synthetic sequence peptides | | | | | |
| TUK-1560 | R- | ILRKLLQE SEQ ID NO: 14 | IV | II | IV |
| TUK-1559 | R- | ILKRLLQE SEQ ID NO: 15 | IV | 0 | IV |
| TUK-1558 | R- | ILRRLLQE SEQ ID NO: 16 | III | 0 | IV |
| TUK-1557 | R- | ILKKLLQE SEQ ID NO: 17 | III+ | 0 | IV |

The sensor also comprises a detectable label. A wide variety of labels may be used including labels providing for direct detection such as radioactivity, luminescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc. In a particular embodiment, the label is differentially detectable according to receptor binding, obviating the need for any bound versus unbound separation step. In a more particular embodiment, the label is a fluorescent label which provides differential fluorescence polarization depending on receptor binding. Exemplary such labels include rhodamine and fluorescein, which may be coupled directly or indirectly though a linker, e.g. an amino acid linker. Suitable labels and methods for peptide conjugation/incorporation (e.g. during solid phase peptide synthesis) are well known in the art. The sensor is generally present at a concentration of less than about 1 $\mu$M, preferably less than about 100 nM, more preferably less than about 10 nM and most preferably less than about 1 nM.

The assay mixture also comprises a candidate agent. Suitable candidate agents encompass numerous chemical classes, though typically they are organic compounds; preferably small organic compounds and are obtained from a wide variety of sources including libraries of synthetic or natural compounds. In a particular embodiment, the assay mixture also comprises a known ligand of the receptor. This embodiment is particularly suitable for screening for antagonists of the receptor. A variety of other reagents may also be included in the mixture. These include reagents like salts, buffers, neutral proteins, e.g. albumin, detergents, protease inhibitors, etc. may be used.

The mixture is incubated under conditions whereby, but for the presence of the candidate agent, the sensor binds the receptor with a reference binding affinity. In a particular embodiment, all the components of the mixture, including the receptor, peptide and agent, are in solution. The mixture components can be added in any order that provides for the requisite bindings and incubations may be performed at any temperature which facilitates optimal binding. Incubation periods are likewise selected for optimal binding but also minimized to facilitate rapid, high-throughput screening. After incubation, the agent-biased binding between the sensor and receptor is detected according to the nature of the label, as described above. A difference in the binding in the presence and absence of the agent indicates that the agent modulates a receptor binding function. A difference, as used herein, is statistically significant and preferably represents at least a 50%, more preferably at least a 90% difference.

The invention also provides reagents for use in the subject methods. For example, the invention provides sensors consisting of, or consisting essentially of, a peptide comprising the sequence $L_1X_1X_2L_2L_3$ SEQ ID NO: 18 covalently coupled to a detectable label, wherein $L_1$–$L_3$ are independently selected from hydrophobic amino acids and $X_1$–$X_2$ are independently selected from any amino acid and wherein the peptide provides direct, in vitro ligand-dependent binding to a nuclear hormone receptor. In a particular embodiment, the label is a fluorescent label coupled to the N-terminus of the peptide and the peptide is 24, preferably 18, more preferably 12, most preferably 8 or fewer residues in length. The invention also provides reagent mixtures, such as a mixture consisting essentially of nuclear hormone receptor, a peptide and a candidate agent, wherein the peptide provides direct, in vitro ligand-dependent binding to the receptor, preferably wherein the binding is enhanced in the presence of the agent.

The following example is offered by way of illustration and not by way of limitation.

EXAMPLE

I. High-Throughput In Vitro Fluorescence Polarization Assay

Reagents:
    Sensor: Rhodamine-labeled $L_1X_1X_2L_2L_3$ peptide (final conc.=1–5 nM)
    Receptor: Glutathione-S-transferase/nuclear hormone receptor ligand binding domain fusion protein (final conc.=100–200 nM)
    Buffer: 10 mM HEPES, 10 mM NaCl, 6 mM magnesium chloride, pH 7.6

Protocol:
1. Add 90 microliters of peptide/NHR mixture to each well of a 96-well microtiter plate.
2. Add 10 microliters of test compound per well.
3. Shake 5 min and within 5 minutes determine amount of fluorescence polarization by using a Fluorolite FPM-2 Fluorescence Polarization Microtiter System (Dynatech Laboratories, Inc).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An in vitro fluorescent polarization assay method for characterizing an agent as a ligand of a nuclear hormone receptor, comprising steps:

forming an in vitro mixture comprising a purified nuclear hormone receptor, a sensor and a candidate agent, but not a natural coactivator protein of the receptor, the sensor consisting of a peptide comprising the sequence $L_1X_1X_2L_2L_3$ (SEQ ID NO: 18) covalently coupled to a directly detectable fluorescent label, wherein $L_1$–$L_3$ are independently selected from hydrophobic amino acids and $X_1$–$X_2$ are independently selected from any amino acid and wherein the peptide provides direct, in vitro ligand-dependent binding to the receptor and is 24 or fewer residues in length, wherein the sensor is at a concentration of less than about 100 nM.;

measuring an assay fluorescence polarization of the sensor as an indication of sensor binding to the receptor in the presence of the agent;

comparing the assay fluorescence polarization to a corresponding control fluorescence polarization, wherein the control fluorescence polarization provides an indication of sensor binding to the receptor in the absence of the agent, and wherein a greater assay fluorescence polarization than control fluorescence polarization indicates that the agent is a ligand of the receptor.

2. A method according to claim 1, wherein the peptide comprises a sequence selected from the group consisting of: KLVQLLTTT (SEQ ID NO:1), ILHRLLQE (SEQ ID NO:2), LLRYLLDK (SEQ ID NO:3), LLRYLLD (SEQ ID NO:4), LRYLLD (SEQ ID NO:5), LLRYLL (SEQ ID NO:6), LRYLL (SEQ ID NO:7), LLRYLLDKD (SEQ ID NO:8), QLLRYLLDKD (SEQ ID NO:9), HQLLRYLLDKD (SEQ ID NO:10), PQAQQKSLLQQLLT (SEQ ID NO:11), LLQQLLTE (SEQ ID NO:12), VTLLQLLLG (SEQ ID NO:13), ILRKLLQE (SEQ ID NO:14, ILKRLLQE (SEQ ID NO:15), ILRRLLQE (SEQ ID NO:16) and ILKKLLQE (SEQ ID NO:17).

3. A method according to claim 1, wherein the peptide consists of a sequence selected from the group consisting of: KLVQLLTTT (SEQ ID NO:1), ILHRLLQE (SEQ ID NO:2), LLRYLLDK (SEQ ID NO:3), LLRYLLD (SEQ ID NO:4), LRYLLD (SEQ ID NO:5), LLRYLL (SEQ ID NO:6), LRYLL (SEQ ID NO:7), LLRYLLDKD (SEQ ID NO:8), QLLRYLLDKD (SEQ ID NO:9), HQLLRYLLDKD (SEQ ID NO:10), PQAQQKSLLQQLLT (SEQ ID NO:11), LLQQLLTE (SEQ ID NO:12), VTLLQLLLG (SEQ ID NO:13), ILRKLLQE (SEQ ID NO:14, ILKRLLQE (SEQ ID NO:15), ILRRLLQE (SEQ ID NO:16) and ILKKLLQE (SEQ ID NO:17).

4. A method according to claim 1, wherein the sensor is at a concentration of less than about 10 nM.

5. A method according to claim 1, wherein the peptide is 12 or fewer residues in length.

6. A method according to claim 1, wherein the fluorescent label is coupled to the N-terminus of the peptide.

7. A method according to claim 2, wherein the sensor is at a concentration of less than about 10 nM.

8. A method according to claim 2, wherein the peptide is 12 or fewer residues in length.

9. A method according to claim 2, wherein the fluorescent label is coupled to the N-terminus of the peptide.

10. A method according to claim 3, wherein the sensor is at a concentration of less than about 10 nM.

11. A method according to claim 3, wherein the peptide is 12 or fewer residues in length.

12. A method according to claim 3, wherein the fluorescent label is coupled to the N-terminus of the peptide.

13. A method according to claim 4, wherein the peptide is 12 or fewer residues in length.

14. A method according to claim 4, wherein the fluorescent label is coupled to the N-terminus of the peptide.

15. A method according to claim 13, wherein the fluorescent label is coupled to the N-terminus of the peptide.

16. A method according to claim 1, wherein the sensor is at a concentration less than that of the receptor.

17. A method according to claim 1, wherein the sensor is at a concentration less than that of the receptor, wherein the sensor is at a concentration of 1–5 nM and the receptor is at concentration of 100–200 nM.

18. A method according to claim 6, wherein the sensor is at a concentration less than that of the receptor, wherein the sensor is at a concentration of 1–5 nM and the receptor is at concentration of 100–200 nM.

* * * * *

SEQUENCE LISTING

<160> NUMBER OF SEQ ID NOS: 18

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: NHR Sensor
 Peptides

<400> SEQUENCE: 1

Lys Leu Val Gln Leu Leu Thr Thr Thr
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: NHR Sensor
    Peptides

<400> SEQUENCE: 2

Ile Leu His Arg Leu Leu Gln Glu

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 3

Leu Leu Arg Tyr Leu Leu Asp Lys
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 4

Leu Leu Arg Tyr Leu Leu Asp
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 5

Leu Arg Tyr Leu Leu Asp
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 6

Leu Leu Arg Tyr Leu Leu
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 7

Leu Arg Tyr Leu Leu
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: NHR Sensor Peptides

<400> SEQUENCE: 8

Leu Leu Arg Tyr Leu Leu Asp Lys Asp
 1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 9

Gln Leu Leu Arg Tyr Leu Leu Asp Lys Asp
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 10

His Gln Leu Leu Arg Tyr Leu Leu Asp Lys Asp
 1               5                  10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 11

Pro Gln Ala Gln Gln Lys Ser Leu Leu Gln Gln Leu Leu Thr
 1               5                  10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 12

Leu Leu Gln Gln Leu Leu Thr Glu
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 13

Val Thr Leu Leu Gln Leu Leu Leu Gly
 1               5

<210> SEQ ID NO 14

```
<211> LENGTH: 8
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 14

Ile Leu Arg Lys Leu Leu Gln Glu
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 15

Ile Leu Lys Arg Leu Leu Gln Glu
 1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 16

Ile Leu Arg Arg Leu Leu Gln Glu
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: NHR Sensor
      Peptides

<400> SEQUENCE: 17

Ile Leu Lys Lys Leu Leu Gln Glu
 1               5

<210> SEQ ID NO 18
<211> LENGTH: 5
<212> TYPE: PRT
<213> ORGANISM: Artificial Sequence
<220> FEATURE:
<221> NAME/KEY: DOMAIN
<222> LOCATION: (1)..(5)
<223> OTHER INFORMATION: Description of Artificial Sequence: NHR Sensor
      Peptides; first, fourth and fifth residue are independently
      selected from hydrophobic amino acids; second and third residues
      are independently selected from any amino acid.

<400> SEQUENCE: 18

Xaa Xaa Xaa Xaa Xaa
 1               5
```